US006437125B1

(12) United States Patent
Geen et al.

(10) Patent No.: US 6,437,125 B1
(45) Date of Patent: Aug. 20, 2002

(54) PROCESS FOR THE PRODUCTION OF PURINE DERIVATIVES

(75) Inventors: Graham Richard Geen, Dunmow; Andrew Colin Share, Saffron Walden, both of (GB)

(73) Assignee: Novartis International Pharmaceutical Ltd., Hamilton (BM)

( * ) Notice: Subject to any disclaimer, the term of this patent is extended or adjusted under 35 U.S.C. 154(b) by 0 days.

(21) Appl. No.: 09/623,700

(22) PCT Filed: Mar. 30, 1999

(86) PCT No.: PCT/EP99/02309

§ 371 (c)(1),
(2), (4) Date: Nov. 1, 2000

(87) PCT Pub. No.: WO99/51604

PCT Pub. Date: Oct. 14, 1999

(30) Foreign Application Priority Data

Apr. 2, 1998 (GB) ................................... 9807116

(51) Int. Cl.[7] .................. C07D 473/32; C07D 473/18; C07D 473/134; C07D 473/16; C07D 473/04

(52) U.S. Cl. .................. 544/276; 544/229; 544/244; 544/264; 544/265; 544/267; 544/273; 544/277

(58) Field of Search .................. 544/229, 244, 544/264, 265, 267, 273, 276, 277

(56) References Cited

U.S. PATENT DOCUMENTS

| 5,684,153 A | 11/1997 | Geen et al. | 544/276 |
| 5,688,948 A | * 11/1997 | Izawa | 544/276 |
| 6,252,075 B1 | * 6/2001 | Shiragami et al. | 544/276 |

FOREIGN PATENT DOCUMENTS

| EP | 0 141 927 A2 | 5/1985 |
| EP | 0 182 024 A2 | 5/1986 |
| EP | 0 352 953 A2 | 1/1990 |
| WO | WO 95/28402 | 10/1995 |

OTHER PUBLICATIONS

Gunderson, Acta Chem. Scan 46, 761, 1992.*
Choudary, et al., "A Direct Approach to the synthesis of Famciclovir and Penciclovir," *Nucleosides& Nucleotides*15(5): 981–994 (1996).
Leonard, et al., "Intramolecular Mechanism of the Allylic Rearrangement From..., "J Amer Chem Soc. 96(18): 5894–5902, (1974).

* cited by examiner

*Primary Examiner*—Mark L Berch
(74) *Attorney, Agent, or Firm*—Thomas R. Savitsky

(57) ABSTRACT

The invention provides a method of rearranging a compound of formula (I), wherein R and R' are selected independently from hydrogen and $C_{1-12}$alkyl; and $R_1$ and $R_2$ are selected independently from hydrogen, hydroxy, halo, $C_{1-12}$alkyl- or aryl carbonate, amino, mono- or di-$C_{1-12}$alkylamino, $C_{1-12}$alkyl or arylamido, $C_{1-12}$alkyl- or arylcarbonyl, $C_{1-12}$alkyl- or arylcarboxy, $C_{1-12}$alkyl- or arylcarbamoyl, $C_{1-12}$alkyl, $C_{2-12}$alkenyl, $C_{2-12}$alkynyl, aryl, heteroaryl, $C_{1-12}$alkoxy, aryloxy, azido, $C_{1-12}$alkyl- or arylthio, $C_{1-12}$alkyl- or arylsulfonyl, $C_{1-12}$alkyl- or arylsilyl, $C_{1-12}$alkyl- or arylphosphoryl, and phosphato; to form a compound of formula (II), wherein R, R', $R_1$ and $R_2$ are as defined for formula (I); said method comprising treating the compound of formula (I) with a palladium (0) catalyst and a (diphenylphosphino)$_n$$C_{1-6}$ alkane, wherein n is an integer of 1–6. The invention also provides methods of R making penciclovir and famciclovir using this rearrangement reaction.

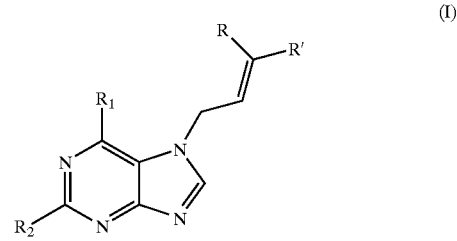

(I)

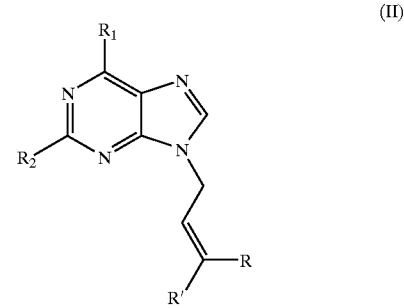

(II)

12 Claims, No Drawings

PROCESS FOR THE PRODUCTION OF PURINE DERIVATIVES

This application is the §371 national stage entry of PCT/EP99/02309, filed Mar. 30, 1999.

The present invention relates to a novel process for the production of N-9 alkylated purine derivatives. In particular the present invention relates to a rearrangement reaction of N-7 alkylated to N-9 alkylated purine derivatives.

Nucleosides and Nucleotides, 15(5), 981–994 (1996) and WO 95/28404 disclose a process for the manufacture of the anti-viral agents 9-(4-acetoxy-3-acetoxymethylbut-1-yl)-2-aminopurine (famciclovir) and 9-(4-hydroxy-3-hydroxymethylbut-1-yl)guanine (penciclovir). According to this process, the 'bromotriester' route, 2-amino-6-chloropurine is reacted with triethyl 3-bromopropane-1,1,1-tricarboxylate in the presence of base to form diethyl 2-[2-(2-amino-6-chloropurin-9-yl)ethyl]-2-carbethoxymalonate. The crude isolate from this alkylation reaction is then treated with sodium methoxide in methanol to form dimethyl 2-[2-(2-amino-6-chloropurin-9-yl)ethyl] malonate. This product is purified by crystallisation and then successively reduced using sodium borohydride and O-acetylated to give 9-(4-acetoxy-3-acetoxymethylbutyl)-2-amino-6-chloropurine. Famciclovir is produced directly from the latter compound by hydrogenation over a supported palladium catalyst; and penciclovir is produced from this compound by acid hydrolysis of the acetoxy groups.

A disadvantage of this route to famciclovir and penciclovir is that the initial alkylation reaction with the bromotriester reagent gives a mixture of the N-9 and N-7 isomers. 2-Amino-6-chloropurine is a fairly expensive starting material, and accordingly the wastage arising from the production of the unwanted N-7 isomer is undesirable.

EP-A-0352953 discloses a process for the production of purine derivatives according to the bromotriester route in which the ratio of N-9 to N-7 products is improved by converting the 2-amino-6-chloropurine to the analogous 6-iodo, 6-benzylthio or 6-(phenacylmethyl)thio compound.

Whilst the process of EP-A-0352953 represents an improvement in the bromotriester process for producing famciclovir, it suffers from the disadvantages that a material quantity of the N-7 isomer still results, and moreover an additional step of converting the 6-chloro substituent to 6-iodo, 6-benzylthio or 6-(phenacylmethyl)thio is required.

Co-pending application GB 9807114.5 discloses a method of making purine derivatives which comprises reacting 2-amino-6-chloropurine with an allyl derivative in the presence of a palladium(0) catalyst and a suitable ligand. This reaction effects N-alkylation of the purine, which proceeds with reasonable regioselectivity in favour of the N-9 isomer, however, it is still desirable to optimise the selectivity of the alkylation in favour of the N-9 isomer over the N-7 isomer.

We have now discovered experimental conditions which greatly enhance this selectivity. In particular, we have found a method of procuring the rearrangement of N-7 alkylated purine derivatives to the N-9 alkylated analogues.

According to the invention therefore there is provided a method of rearranging a compound of formula (I):

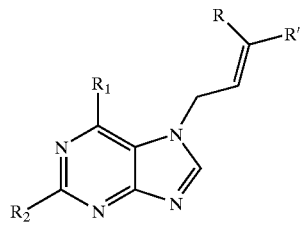

wherein R and R' are selected independently from hydrogen and $C_{1-12}$alkyl; and $R_1$ and $R_2$ are selected independently from hydrogen, hydroxy, halo, $C_{1-12}$alkyl- or arylcarbonate, amino, mono- or di-$C_{1-12}$alkylamino, $C_{1-12}$alkyl or arylamido, $C_{1-12}$alkyl- or arylcarbonyl, $C_{1-12}$alkyl- or arylcarboxy, $C_{1-12}$alkyl- or arylcarbamoyl, $C_{1-12}$alkyl, $C_{2-12}$alkenyl, $C_{2-12}$alkynyl, aryl, heteroaryl, $C_{1-12}$alkoxy, aryloxy, azido, $C_{1-12}$alkyl- or arylthio, $C_{1-12}$alkyl- or arylsulfonyl, $C_{1-12}$alkyl- or arylsilyl, $C_{1-12}$alkyl- or arylphosphoryl, and phosphato;

to form a compound of formula (II):

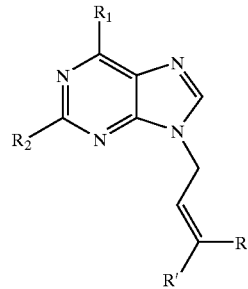

wherein R, R', $R_1$ and $R_2$ are as as defined for formula (I); said method comprising treating the compound of formula (I) with a palladium (0) catalyst and a (diphenylphosphino)$_n$C$_{1-6}$alkane, wherein n is an integer of from 1–6.

Any of R, R', $R_1$ and $R_2$, when other than H, may be unsubstituted or substituted by one or more groups selected independently from hydroxy, halo, $C_{1-12}$alkyl- or aryl carbonate, amino, mono- or di- $C_{1-12}$alkylamino, $C_{1-12}$alkyl- or arylamido, $C_{1-12}$alkyl- or arylcarbonyl, $C_{1-12}$alkyl- or arylcarboxy, $C_{1-12}$alkyl- or arylcarbamoyl, $C_{1-12}$alkyl, $C_{1-12}$alkenyl, $C_{1-12}$alkynyl, aryl, heteroaryl, $C_{1-12}$alkoxy, aryloxy, azido, $C_{1-12}$alkyl- or arylthio, $C_{1-12}$alkyl- or arylsulfonyl, $C_{1-12}$alkyl- or arylsilyl, $C_{1-12}$alkyl- or arylphosphoryl, and phosphato.

The palladium (0) catalyst may be a palladium (0) dibenzylidene catalyst. In a preferred embodiment of the invention the catalyst is a tris(dibenzylidene) dipalladium (0) catalyst, e.g. tris(dibenzylidene) dipalladium (0) chloroform.

The palladium (0) catalyst may be formed in situ from a palladium (II) source such as palladium acetate, or may be added to the reaction as another form of palladium (0), e.g. tetrakis(triphenylphosphine) palladium (0).

The (diphenylphosphino)$_n$C$_{1-6}$alkane ligand is preferably a bis(diphenylphosphino)C$_{1-6}$alkane such as 1,2-bis(diphenylphosphino)ethane or 1,3-bis(diphenylphosphino)propane.

The rearrangement reaction of the invention may be conducted at a temperature in the range of about 40°–120° C., preferably about 60°–100° C., and typically about 80° C.

The reaction may be conducted for a period of 1 to 24 hours, preferably 1–12 hours, typically about 4 hours.

The rearrangement reaction of the invention may be carried out in an inert solvent. The inert solvent may be selected from dimethylformamide (DMF), diethylformamide, dimethylacetamide and aqueous dimethylformamide. DMF is preferred.

The reaction may be conducted under an inert atmosphere. Any suitable inert gas may be used, but argon is preferred. Preferably the reaction is carried out under a flow of the inert gas.

$R_1$ is preferably halo, typically chloro.

$R_2$ is preferably an amino group. The amino group may be protected throughout using conventional protecting groups such as benzyl, acetyl or a Schiff's base.

R and R' are preferably $CH_2OR_3$ and $CH_2OR_4$ respectively, wherein $R_3$ and $R_4$ are selected independently from $C_{1-12}$alkyl, aryl, $C_{1-12}$alkylaryl, $C_{1-12}$alkylsilyl, arylsilyl and $C_{1-12}$alkylarylsilyl, or $R_3$ and $R_4$ are joined together to form a cyclic acetal or ketal.

Thus the side-chain on N-7 of formula (I) is preferably a 4-alkoxy-3-alkoxymethyl but-2-enyl group of formula (III):

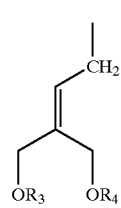

(III)

$R_3$ and $R_4$ may be selected independently from benzyl and $C_{1-12}$alkyldiphenylsilyl, e.g. t-butyldiphenylsilyl. Preferably however, $R_3$ and $R_4$ are linked to form a six membered cyclic acetal or ketal of formula (IV):

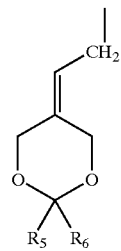

(IV)

wherein $R_5$ and $R_6$ are selected independently from H, $C_{1-12}$alkyl, and aryl.

Preferably $R_5$ and $R_6$ are both $C_{1-12}$alkyl, more preferably $R_5$ and $R_6$ are both methyl.

Thus, in one embodiment of the invention, the rearrangement of the compound of formula (I) to the compound of formula (II) proceeds as follows:

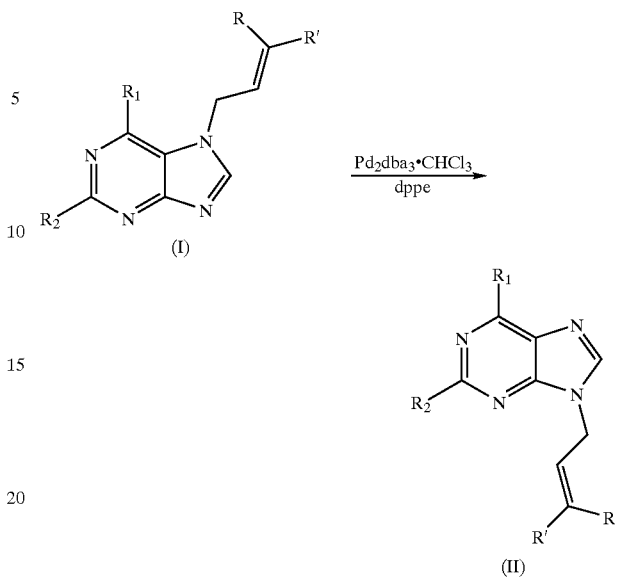

The compound of formula (I) may be introduced as such to the reaction mixture. Alternatively, the compound of formula (I) may be formed in situ by the reaction of a compound of formula (V):

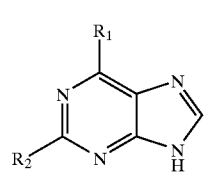

(V)

wherein $R_1$ and $R_2$ are as defined for formula (I), with a compound of formula (VI):

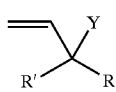

(VI)

wherein Y is a leaving group and R and R' are as defined for formula (I), in the presence of the dipalladium (0) catalyst and (diphenylphosphino)$_n$C$_{1-6}$alkane.

Preferably, the reaction between the compound of formula (V) and the compound of formula (VI) is conducted in the presence of a base. The base may be selected from caesium carbonate, sodium carbonate, potassium carbonate, lithium carbonate, cesium fluoride, lithium hydride, sodium hydride, sodium hydroxide, triethylamine, diazabicyclo [5.4.0] undec-7-ene and 1,1,3,3-tetramethylguanidine. Preferably however the base is caesium carbonate.

Various of the compounds of formula (VI) are novel, thus according to a further aspect of the invention there is provided a compound of formula (VI):

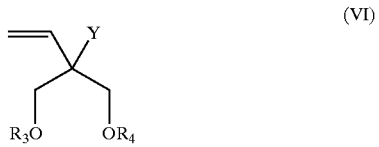

(VI)

wherein Y is a leaving group and $R_3$ and $R_4$ are are joined together to form a cyclic acetal or ketal.

A preferred group of compounds of formula (VI) are those of formula (VII):

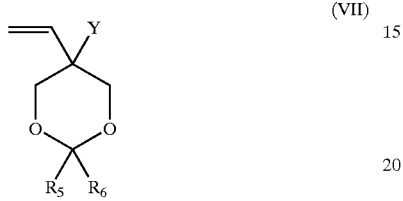

(VII)

wherein Y is a leaving group and $R_5$ and $R_6$ are selected independently from H, $C_{1-12}$alkyl and aryl. Preferably $R_5$ and $R_6$ are both $C_{1-12}$alkyl, more preferably $R_5$ and $R_6$ are both methyl.

A particular compound of formula (VI) that may be mentioned is methyl 2,2-dimethyl-5-ethenyl-1,3-dioxane-5-carbonate.

The compounds of formula (VI) may be prepared by reacting a compound of formula (VIII):

(VIII)

wherein R and R' are as defined for formula (I), with a vinyl carbanion and thereafter converting the resulting alkoxide to the leaving group Y.

The vinyl carbanion may be a Grignard reagent such as vinylmagnesium bromide.

The nucleophilic addition of the vinyl carbanion to the compound of formula (VIII) may be carried out in an inert solvent such as tetrahydrofuran, at a temperature of less than about −60° C., preferably about −78° C.

The leaving group Y may be selected from the group consisting of $C_{1-6}$alkyl- or aryl carbonates, e.g. methyl carbonate or phenyl carbonate; $C_{1-6}$acyloxy e.g. acetate or trifluoroacetate; or $C_{1-6}$alkylphosphates. e.g. diethylphosphate. A $C_{1-6}$alkyl carbonate is preferred however, because it gives rise to volatile side products when reacted with the compound of formula (V). The leaving group may be introduced by, for example, quenching the reaction between the compound of formula (VIII) and vinyl carbanion with a $C_{1-6}$alkyl chloroformnate, e.g. methyl chloroformate, if desired. The 5-vinyl-5-hydroxy intermediate formed by reaction of the vinyl carbanion with the compound of formula (VIII) may be isolated before the leaving group Y is introduced. The compound of formula (VI) may be isolated and purified by known methods. Alternatively, the compound of (VI) may be used as a crude oil without purification.

In another aspect of the invention there is provided a process for the production of a compound of formula (IX):

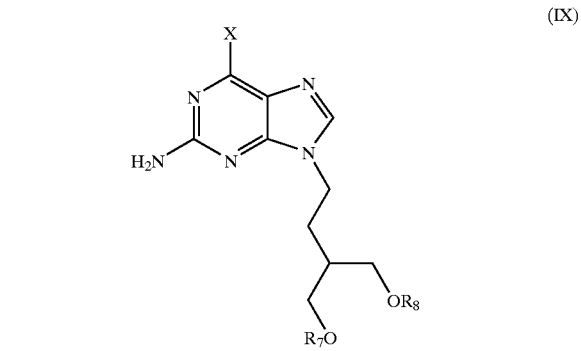

(IX)

wherein X is H or OH; and $R_7$ and $R_8$ are independently selected from H and $R_9CO$ wherein $R_9$ is phenyl, $C_{1-12}$alkyl or phosphoryl; which process comprises rearranging a compound of formula (I) in which $R_1$ and $R_2$ are as defined for formula (I), and R and R' are respectively $CH_2OR_3$ and $CH_2OR_4$ as defined for formula (III), to form a compound of formula (II) according to the process of the invention defined above; hydrogenating the compound of formula (II); converting —$OR_3$ and —$OR_4$ to form two hydroxy groups; and thereafter if and as necessary:

(i) converting one or both of the hydroxy groups on the resulting 4-hydroxy-3-hydroxymethylbutyl to form compounds where $R_7$ and $R_8$ represent $R_9CO$; and/or (ii) converting $R_1$ to X and $R_2$ to $NH_2$.

Preferably $R_7$ and $R_8$ are both hydrogen or acetyl. When X is H and $R_7$ and $R_8$ are both acetyl the compound of formula (IX) is famciclovir. When X is OH and $R_7$ and $R_8$ are both H, the compound of formula (IX) is penciclovir.

Hydrogenation of the ethylidene moiety may be effected by hydrogenation of the compound of formula (II) in the presence of a catalyst, preferably a palladium catalyst, such as palladium on charcoal. Other suitable catalysts are Pd/CaCO$_3$ and Pd(OH$_2$)/C. The hydrogenation may be carried out in a solvent selected from the group consisting of alkyl esters e.g. ethyl acetate, tetrahydrofuran, and $C_{1-6}$alkylalcohols e.g. methanol or ethanol.

Optionally a base is included in the reaction mixture. The base may be selected from triethylamine, sodium acetate, potassium hydroxide, aqueous sodium hydroxide and basic alumina. Alternatively, a basic ion exchange resin may be employed. Hydrogenation may be carried out at an elevated temperature and pressure or, alternatively, at room temperature and atmospheric pressure. As mentioned above, $R_1$ is preferably halo such as chloro. In accordance with an important aspect of the invention, hydrogenation of the compound of formula (II) in the presence of a base reduces both the chloro moiety (to H) at the 6-position on the purine ring and also the double bond. This one step reduction of the 6-chloro and ethylidene groups represents a particularly advantageous synthetic route to famciclovir. The reduced product may be isolated if required. In the absence of base, only the double bond is reduced. Subsequent hydrolysis of the 6-chloro group and —$OR_3$ and —$OR_4$ then affords penciclovir. Therefore, the choice of whether or not to use a base allows the synthesis of either famciclovir or penciclovir.

—$OR_3$ and —$OR_4$ may be converted to —OH by any suitable method known to those skilled in the art such as those described in EP 141927. Cyclic acetals or ketals are preferably hydrolysed using tetrahydrofuran/methanol and hydrochloric acid. Where $R_1$ and $R_2$ are benzyl, then hydrogenation may be used.

In a particularly preferred embodiment of this aspect of the invention, the two hydroxy groups of the 4-hydroxy-3-hydroxymethylbut-1-yl group are acylated. Any convenient acylation method known to those skilled in the art may be used, such as those described in EP 182024, preferably acetic anhydride is employed.

Unless otherwise stated, any of the alkyl groups mentioned above may comprise 1–12 carbon atoms, preferably 1–6 carbon atoms. Alkyl groups may be straight or branched chain or cyclic. Cyclic alkyl groups preferably comprise 3–8 carbon atoms. Any alkyl groups may be substituted by one or more fluoro atoms. Alkenyl and alkynyl groups should be construed accordingly.

Any of the aryl groups mentioned above preferably comprise 5–10 carbon atoms and may be mono- or bicyclic. Suitable aryl groups included phenyl and naphthyl, preferably phenyl.

Any of the heteroaryl groups mentioned above preferably comprise 5–10 carbon atoms, may be mono- or bicyclic and contain 1, 2 or 3 heteroatoms selected from oxygen, nitrogen and sulphur.

All publications, including but not limited to patents and patent applications, cited in this specification are herein incorporated by reference as if each individual publication were specifically and individually indicated to be incorporated by reference herein as though fully set forth.

There follows a description by way of example only of embodiments of the present invention.

EXAMPLE 1

Preparation of Methyl 2,2-Dimethyl-5-ethenyl-1,3-dioxane-5-carbonate 2,2-Dimethyl-1,3-dioxan-5-one (38.0 g) in tetrahydrofuran (250 ml) was added dropwise to a 1M solution of vinylmagnesium bromide in tetrahydrofuran (700 ml) under argon maintaining a temperature of less than −60° C. The reaction mixture was cooled to −78° C. and stirred at this temperature for 30 min. Methyl chloroformate (75 ml) was added dropwise and the resulting mixture stirred at −78° C. for 15 min before being allowed to warm to room temperature. The solvent was removed by evaporation under reduced pressure. Ethyl acetate (2×500 ml) was added to the residue and the solvent removed by distillation after each addition. The residue was stiffed in ethyl acetate/hexane 40:60 and the resulting mixture passed through a short silica column. The column was washed with further ethyl acetate/hexane 40:60 (2×1.0 L) and the combined fractions concentrated to give an oil. The crude oil was purified by silica column chromatography (eluent hexane/ethyl acetate 90:10 increasing to hexane/ethyl acetate 85:15) to give the title compound as a pale yellow oil (46 g, 73% yield).

$^1$Hnmr (CDCl$_3$): δ6.0 (dd, 1H, CH); 5.3 (m, 2H, CH$_2$); 4.05 (abq, 4H, 2×CH$_2$); 3.75 (s, 3H, OCH$_3$); 1.45 (s, 3H, CH$_3$); 1.4 (s, 3H, CH$_3$).

EXAMPLE 2

Example 1 was repeated except that, as an alternative to purification by column chromatography, the methyl 2,2-dimethyl-5-ethenyl-1,3-dioxane-5-carbonate was purified by distillation at 78° C. and 0.6 mmHg.

EXAMPLE 3

Example 1 was repeated, except that the reaction mixture was poured into 1M potassium dihydro-orthophosphate then extracted into diethyl ether and purified by column chromatography.

EXAMPLE 4

Example 1 was repeated, except that the reaction mixture was concentrated and the residue slurried in diethyl ether and saturated brine. The ether layer was concentrated, and the residue purified by column chromatography.

EXAMPLE 5

Preparation of 5-[2-(2-Amino-6-chloropurin-9-yl)]ethylidene-2,2-dimethyl-1,3-dioxane 2-Amino-6-chloropurine and methyl 2,2-dimethyl-5-ethenyl-1,3-dioxane-5-carbonate were suspended in DMF and degassed under high vacuum for 15 min. To the reaction was added cesium carbonate, 1,2-bis(diphenyl-phosphino) ethane [DIPHOS] and Pd$_2$dba$_3$.CHCl$_3$ as a palladium (0) source. The reaction was degassed a second time then stirred at 60° C. overnight under a flow of argon. The reaction was worked up by evaporating the solvent and crystallising the residue from methanol to give the title compound (61% yield).

$^1$Hnmr (DMSO-d$_6$): δ8.1 (s, 1H, CH); 6.9 (s, 2H, NH$_2$); 5.5 (t, 1H, CH); 4.6 (d, 2H, CH$_2$); 4.5 (s, 2H, CH$_2$); 4.2 (s, 2H, CH$_2$); 1.3 (s, 6H, 2×CH$_3$); m.p. 157–159° C.

EXAMPLE 6

Preparation of 5-[2-(2-Aminopurin-9-yl)ethyl]-2,2-dimethyl-1,3-dioxane

A mixture of 5-[2-(2-amino-6-chloropurin-9-yl)]ethylidene-2,2-dimethyl-1,3-dioxane (0.45 g), 5% palladium on carbon (0.225 g) and triethylamine (0.22 ml) in ethyl acetate (22.5 ml) was hydrogenated at 50° C. for 18 hours at 50 p.s.i. The catalyst was removed by filtration and the filter washed with ethyl acetate. The combined filtrate and wash were concentrated under reduced pressure to give a gum which was purified by silica gel chromatography (eluted with dichloromethane/methanol 99:1 increasing to 97:3) to give the title compound (300 mg, 74% yield).

$^1$Hnmr (DMSO-d$_6$): δ8.6 (s, 1H, CH); 8.1 (s, 1H, CH); 6.5 (s, 2H, NH$_2$), 4.1 (t, 2H, CH$_2$); 3.8–3.5 (m, 4H, 2×CH$_2$); 1.73 (q, 2H, CH$_2$); 1.6 (m, 1H, CH); 1.3 (s, 3H, CH$_3$); 1.25 (s, 3H, CH$_3$).

EXAMPLE 7

Preparation of 5-[2-(2-Amino-6-chloropurin-9-yl)ethyl]-2,2-dimethyl-1,3-dioxane

5% Palladium on carbon (1.5 g) in tetrahydrofuran (40 ml) was prehydrogenated for 30 min at 50 p.s.i. 2,2-Dimethyl-5-[2-(2-amino-6-chloropurin-9-yl)]ethylidene-1,3-dioxane (3.0 g) in tetrahydrofuran (80 ml) was added and washed in with tetrahydrofuran (30 ml). The mixture was hydrogenated overnight at 50 p.s.i. with stirring. The catalyst was removed by filtration to give a colourless solution. The solvent was removed under reduced pressure and the residue recrystallised from IPA to give the title compound (1.92 g, 62.2% yield).

$^1$Hnmr (DMSO-d$_6$): δ8.18 (s, 1H, CH); 6.91 (s, 2H, NH$_2$); 4.08 (t, 2H, CH$_2$); 3.8 (dd, 2H, CH$_2$); 3.5 (dd, 2H, CH$_2$); 1.75 (m, 2H, CH$_2$); 1.59 (m, 1H, CH); 1.33 (s, 3H, CH$_3$); 1.27 (s, 3H, CH$_3$).

Analysis: Found C: 50.14; H: 5.88; N: 22.34%; Required: C: 50.08; H: 5.82; N: 22.46%.

5-[2-(2-Amino-6-chloropurin-9-yl)ethyl]-2,2-dimethyl-1,3-dioxane can be converted to penciclovir using techniques known in the art such as those described in EP 141927.

EXAMPLE 8

Preparation of 2-Amino-9-(4-hydroxy-3-hydroxymethylbut-1-yl)purine Hydrochloride To a stirred solution of 2,2-dimethyl-5-[2-(2-aminopurin-9-yl)ethyl]-1,3-dioxane (1 g) in a mixture of tetrahydrofuran (20 ml) and methanol (6 ml) at room temperature was added concentrated hydrochloric acid (0.32 ml). The resulting mixture was stirred for 2 hours during which time a solid crystallised. The solid was collected by filtration, washed with tetrahydrofuran (2 ml) and dried under a flow of air to give the desired product as the hydrochloride salt (800 mg, 81% yield).

$^1$Hnmr (DMSO-$d_6$/$D_2O$): δ8.9 (s, 1H, CH); 8.6 (s, 1H, CH); 4.2 (t, 2H, $CH_2$); 3.5–3.3 (m, 4H, 2×$CH_2$); 1.8 (q, 2H, $CH_2$); 1.5 (m, 1H, CH); m.p. 174–176° C.

EXAMPLE 9

Preparation of 9-(4-Acetoxy-3-acetoxymethylbut-1-yl)-2-aminopurine (Famciclovir)

To a stirred suspension of 2-amino-9-(4-hydroxy-3-hydroxymethylbut-1-yl)purine hydrochloride (0.79 g), 4-dimethylaminopyridine (16 mg) and triethylamine (1.4 ml) in dichloromethane (16 ml) at room temperature was added acetic anhydride (0.57 ml). The resulting mixture was stirred at ambient temperature for 2.25 hours. Methanol (4 ml) was added and the solution stirred for 30 min before being evaporated to dryness. Water (20 ml) was added and the aqueous solution extracted with dichloromethane (3×20 ml). The combined extracts were concentrated to give an oil. This oil was dissolved in 2-propanol (5 ml), the solvent evaporated and the residue recrystallised from 2-propanol (5 ml). The product was collected by filtration, washed with 2-propanol (3 ml) and dried to give the title compound (654 mg, 70%).

$^1$Hnmr (DMSO-$d_6$): δ8.6 (s, 1H, CH); 8.1 (s, 1H, CH); 6.5 (s, 2H, $NH_2$); 4.1 (t, 2H, $CH_2$); 4.0 (d, 4H, 2×$CH_2$); 2.0 (s, 6H, 2×$CH_3$); 1.9 (m, 3H, CH and $CH_2$).

EXAMPLE 10

Rearrangement of 5-[2-(2-Amino-6-chloropurin-7-yl)]ethylidene-2,2-dimethyl-1,3-dioxane 5-[2-(2-Amino-6-chloropurin-7-yl)]ethylidene-2,2-dimethyl-1,3-dioxane was suspended in DMF and degassed under high vacuum for 15 min. To the mixture was added the $Pd_2dba_3 \cdot CHCl_3$ and bis(diphenylphosphino)ethane (DIPHOS). The reaction was degassed for a second time then stirred at 80° C., overnight, under a flow of argon. The solution yield of 5-[2-(2-aminopurin-9-yl)ethyl]-2,2-dimethyl-1,3-dioxane was 60%.

What is claimed is:

1. A method of rearranging a compound of formula (I):

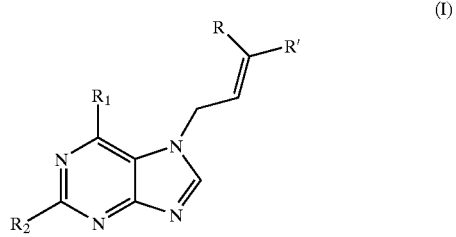

(I)

wherein R and R' are selected independently from hydrogen and $C_{1-12}$alkyl; and $R_1$ and $R_2$ are selected independently from hydrogen, hydroxy, halo, $C_{1-12}$alkyl or aryl carbonate, amino, mono- or di-$C_{1-12}$alkylamino, $C_{1-12}$alkyl- or arylamido, $C_{1-12}$alkyl- or arylcarbonyl, $C_{1-12}$alkyl- or arylcarbamoyl, $C_{1-12}$alkyl, $C_{2-12}$alkenyl, $C_{2-12}$alkynyl, aryl, heteroaryl, $C_{1-12}$alkoxy, aryloxy, azido, $C_{1-12}$alkyl- or arylthio, $C_{1-12}$alkyl- or arylsulfonyl, $C_{1-12}$alkyl- or arylsilyl, and $C_{1-12}$alkyl- or arylphosphoryl;

to form a compound of formula (II):

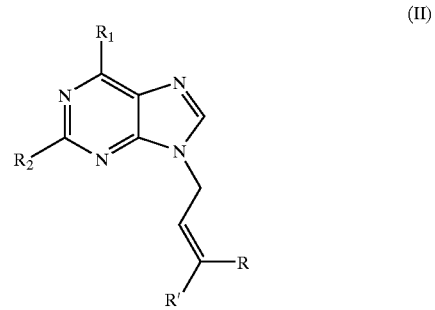

(II)

wherein R, R', $R_1$ and $R_2$ are as defined for formula (I);

said method comprising treating the compound of formula (I) with a palladium (0) catalyst and a (diphenylphosphino)$_n C_{1-6}$alkane, wherein n is an integer of from 1–6.

2. A method as claimed in claim 1, wherein the catalyst is a palladium (0) dibenzylidene catalyst.

3. A method as claimed in claim 1, wherein the (diphenylphosphino)$_n C_{1-6}$alkane is a bis(diphenylphosphino)$C_{1-6}$alkane.

4. A method as claimed in claim 1, wherein the rearrangement reaction is conducted at a temperature in the range of about 40°–120° C.

5. A method as claimed in claim 1, wherein the rearrangement is carried out in an inert solvent under an inert atmosphere.

6. A method as claimed in claim 1, wherein $R_1$ is chloro and $R_2$ is an amino group.

7. A process for the production of a compound of formula (IX):

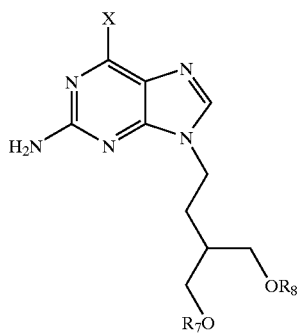

wherein X is H or OH and $R_7$ and $R_8$ are independently selected from H and $R_9CO$ wherein $R_9$ is phenyl, $C_{1-12}$alkyl or phosphoryl; which process comprises rearranging a compound of formula (I):

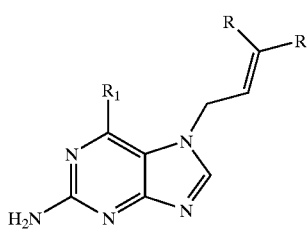

wherein $R_1$ is H, OH or halo, R and R' are respectively $CH_2OR_3$ and $CH_2OR_4$, and $R_3$ and $R_4$ are selected independently from $C_{1-12}$alkyl, aryl, $C_{1-12}$alkylaryl, $C_{1-12}$arylsilyl, and $C_{1-12}$alkylarylsily $R_3$ and $R_4$ are joined together to form a cyclic acetal or ketal;

to form a compound of formula (II):

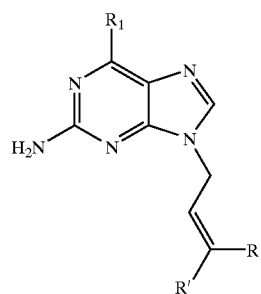

wherein $R_1$, R and R' are as defined above,
said rearranging comprising treating the compound of formula (I) with a palladium (0) catalyst and a (diphenylphosphino)$_n$$C_{1-6}$alkane, wherein n is an integer of from 1 to 6;
converting —$OR_3$ and —$OR_4$ to form two hydroxy groups; and thereafter if and as necessary:
  (i) converting one or both of the hydroxy groups on the resulting 4-hydroxy-3-hydroxymethylbutyl to form compounds where $R_7$ and $R_8$ represent $R_9CO$; and/or
  (ii) converting $R_1$=halo to X=H or OH.

8. A method of rearranging a compound of formula (I)

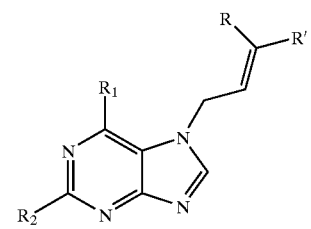

wherein R and R' are $CH_2OR_3$ and $CH_2OR_4$, respectively, $R_3$ and $R_4$ are selected independently from $C_{1-12}$alkyl, aryl, $C_{1-12}$alkylaryl, $C_{1-12}$alkylsilyl, arylsilyl and $C_{1-12}$alkylarylsilyl, or $R_3$ and $R_4$ are joined together to form a cyclic acetal or ketal, and $R_1$ and $R_2$ are selected independently from hydrogen, hydroxy, halo, $C_{1-12}$alkyl- or aryl carbonate, amino, mono- or di-$C_{1-12}$alkylamino, $C_{1-12}$alkyl- or arylamido, $C_{1-12}$alkyl- or arylcarbonyl, $C_{1-12}$alkyl- or arylcarboxy, $C_{1-12}$alkyl- or arylcarbamoyl, $C_{1-12}$alkyl, $C_{2-12}$alkenyl, $C_{2-12}$alkynyl, aryl, heteroaryl, $C_{1-12}$alkoxy, aryloxy, azido, $C_{1-12}$alkyl- or arylthio, $C_{1-12}$alkyl- or arylsulfonyl, $C_{1-12}$alkyl- or arylsilyl, $C_{1-12}$alkyl- or arylphosphoryl, and phosphato;
to form a compound of formula (II):

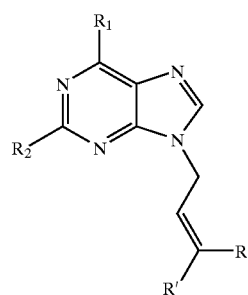

wherein R, R', $R_1$ and $R_2$ are as defined above; said method comprising treating the compound of formula (I) with a palladium (0) catalyst and a (diphenylphosphino)$_n$$C_{1-6}$alkane, wherein n is an integer of from 1–6.

9. A method as claimed in claim 1, wherein the compound of formula (I) is formed in situ by the reaction of a compound of formula (V):

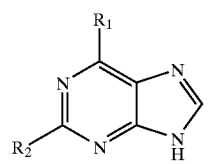

wherein $R_1$ and $R_2$ are as defined in claim 1, with a compound of formula (VI):

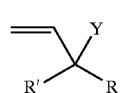

wherein Y is a leaving group and R and R' are as defined in claim 1, in the presence of a palladium (0) catalyst and a (diphenylphosphino)$_n$$C_{1-6}$alkane.

10. A process as claimed in claim 7 wherein $R_1$ is chloro.

11. A process as claimed in claim 7 wherein the compound of formula (IX) is 9-(4-acetoxy-3-acetoxymethylbut-l-yl)-2-aminopurine (famciclovir), or 9-(4-hydroxy-3-hydroxymethylbut-l-yl)guanine (penciclovir).

12. A method as claimed in claim 11, wherein $R_3$ and $R_4$ are linked to form a six membered cyclic acetal or ketal and $R_3$ and $R_4$ together have the formula

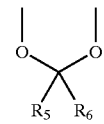

wherein $R_5$ and $R_6$ are selected independently from H, $C_{1-12}$alkyl, and aryl.

* * * * *